(12) United States Patent
Ito

(10) Patent No.: US 9,107,620 B2
(45) Date of Patent: Aug. 18, 2015

(54) HEARING-ABILITY MEASUREMENT DEVICE AND METHOD THEREOF

(75) Inventor: Gempo Ito, Kanagawa (JP)

(73) Assignee: Panasonic Corporation, Osaka (JP)

( * ) Notice: Subject to any disclaimer, the term of this patent is extended or adjusted under 35 U.S.C. 154(b) by 349 days.

(21) Appl. No.: 13/388,352

(22) PCT Filed: Jun. 2, 2011

(86) PCT No.: PCT/JP2011/003112
§ 371 (c)(1),
(2), (4) Date: Feb. 1, 2012

(87) PCT Pub. No.: WO2011/152056
PCT Pub. Date: Dec. 8, 2011

(65) Prior Publication Data
US 2012/0132004 A1 May 31, 2012

(30) Foreign Application Priority Data
Jun. 4, 2010 (JP) .................................. 2010-129085

(51) Int. Cl.
*A61B 5/12* (2006.01)
*H04R 29/00* (2006.01)

(52) U.S. Cl.
CPC ..................................... *A61B 5/123* (2013.01)

(58) Field of Classification Search
CPC .......... A61B 5/121; A61B 5/12; H04R 25/70; H04R 25/606; H04R 25/30; H04R 29/00
USPC ................ 73/585; 600/559; 381/60
See application file for complete search history.

(56) References Cited

U.S. PATENT DOCUMENTS

| | | | | |
|---|---|---|---|---|
| 5,792,072 | A * | 8/1998 | Keefe | 600/559 |
| 7,068,793 | B2 * | 6/2006 | Shim | 381/60 |
| 8,161,816 | B2 * | 4/2012 | Beck | 73/585 |
| 8,777,869 | B2 * | 7/2014 | Givens et al. | 600/559 |

(Continued)

FOREIGN PATENT DOCUMENTS

| | | |
|---|---|---|
| CN | 1850002 | 10/2006 |
| JP | 58-44036 | 3/1983 |

(Continued)

OTHER PUBLICATIONS

Gempo Itoh, et al., "A Study on a method of measuring auditory spectral and temporal resolution for sensorineural hearing-impaired listeners—Measurement of degree of auditory resolution deterioration by F& T test—", IEICE Technical Report, Feb. 25, 2010, vol. 109, No. 451, pp. 105-109 with its English translation.

(Continued)

*Primary Examiner* — J M Saint Surin
(74) *Attorney, Agent, or Firm* — Wenderoth, Lind & Ponack, L.L.P.

(57) ABSTRACT

Provided is a hearing-ability measurement device and a method thereof for measuring a masking curve more correctly and in a shorter time.
A test sound generation unit generates a test sound including a probe and a masker, and outputs the test sound from a test sound output unit. A perception examination unit examines whether or not the subject perceives the probe. An adjustment unit adjusts acoustic properties of the test sound, based on a result of the examination. Here, kinds of adjusted acoustic properties are different between the situation of prove perception success and the situation of prove perception failure. As a result, the masking curve is directly tracked and the measurement is performed more correctly and in a shorter time.

12 Claims, 16 Drawing Sheets

(56) References Cited

U.S. PATENT DOCUMENTS

| | | | |
|---|---|---|---|
| 8,795,192 B2 * | 8/2014 | Allen et al. | 600/559 |
| 2003/0078515 A1 | 4/2003 | Menzel et al. | |
| 2004/0015099 A1 | 1/2004 | Nakaichi et al. | |
| 2008/0008070 A1 | 1/2008 | Kwon | |
| 2009/0306490 A1 * | 12/2009 | Jacobs et al. | 600/365 |
| 2011/0004468 A1 * | 1/2011 | Fusakawa et al. | 704/214 |
| 2013/0303941 A1 * | 11/2013 | Porges et al. | 600/559 |

FOREIGN PATENT DOCUMENTS

| | | |
|---|---|---|
| JP | 6-133953 | 5/1994 |
| JP | 6-327654 | 11/1994 |
| JP | 7-124137 | 5/1995 |
| JP | 7-171138 | 7/1995 |
| JP | 2003-210436 | 7/2003 |
| JP | 3741651 | 2/2006 |

OTHER PUBLICATIONS

B. Larsbv and S. Arlinger, "Auditory temporal and spectral resolution in normal and impaired hearing", J. Am. Acad. Audiol., Apr. 1999, vol. 10. No. 4, pp. 198-210.

Takashi Tsuiki, "Chokaku Kensa No Jissai" (Facts About Hearing Tests), 2nd ed., Nanzando Co., Ltd., pp. 62-67, Feb. 5, 2004 with its English translation.

Office Action with Search Report mailed Apr. 14, 2014 in corresponding Chinese Application No. 201180003133.9, with English translation of Search Report.

Extended European Search Report mailed Aug. 6, 2014 in European Patent Application No. 11789469.1.

Birgitta Larsby et al., "A Method for Evaluating Temporal, Spectral and Combined Temporal-Spectral Resolution of Hearing", Scandinavian Audiology Scandinavian University Press Norway, vol. 27, No. 1, 1998, pp. 3-12, XP8170927.

Janne V. Kujala et al., "Bayesian adaptive estimation: The next dimension", Journal of Mathematical Psychology, vol. 50, No. 4, Aug. 2006, pp. 369-389, XP024949630.

International Search Report issued Jul. 5, 2011 in International (PCT) Application No. PCT/JP2011/003112 (English language version).

Brian C. J. Moore, "Cochlear Hearing Loss", 2nd Edition, John Wiley and Sons, Ltd., Dec. 2007, pp. 36, 37, 44, 90, 91, 114, 115, 140, 141, and 232.

* cited by examiner

■ Changes in Three-Dimensional Masking Curve caused by Changes in Masker Level (Embodiment 4)

HEARING-ABILITY MEASUREMENT DEVICE AND METHOD THEREOF

TECHNICAL FIELD

The present invention relates to devices and methods for measuring human hearing-ability.

BACKGROUND ART

Presently, general hearing ability tests for hearing-impaired people are for examining a hearing threshold level (a pure-tone threshold) by using an audiometer. The hearing threshold tests can check a minimum audible level for each frequency. However, the mechanism of hearing impairment is complicated, which is considered as causing various changes in auditory property, such as loudness recruitment, spectral/temporal masking increase as well as hearing threshold level decrease (see Non Patent Literature 1).

An example of devices for detecting the above-described auditory property changes is a device that estimates a shape of an auditory filter related closely to spectral masking (see Patent Literature 1).

This device uses a masker which is added with a spectral gap (i.e. silent part generated on a frequency axis) and a probe. After setting presentation levels of the masker and the probe, a width of the spectral gap is gradually increased. While gradually increasing the spectral gap width, it is observed whether or not the probe can be heard. Thereby, a minimum spectral gap width by which the probe is heard is measured. Then, depending on a numeral value of the measured spectral gap width, the shape of the auditory filter is estimated using a conversion formula.

Another disclosed example is a device that measures both spectral masking and temporal masking (see Non Patent Literature 2).

This device uses a masker and a probe which are added with one or both of the spectral gap and the temporal gap (i.e silent part generated on a time axis). After setting a presentation level of the masker, a spectral gap width, and a temporal gap width, it is observed whether or not the probe can be heard while varying the presentation level of the probe. Thereby, a minimum presentation level of the probe by which the probe is heard is measured.

CITATION LIST

Patent Literatures

[PTL 1] Japanese Patent Publication No. 3741651

Non Patent Literature

[NPL 1] B. C. J Moore, "Cochlear hearing loss", 2nd ed., John Wiley & Sons Ltd., 2007
[NPL 2] B. Larsby and S. Arlinger, "Auditory temporal and spectral resolution in normal and impaired hearing", J. Am. Acad. Audiol., 1999, vol. 10, no. 4, pp. 198-210
[NPL 3] Takashi Tachiki (editor), "Choulkaku kensa no jissai", 2nd ed., pp. 62-67, Feb. 5, 2004

SUMMARY OF INVENTION

Problems that Invention is to Solve

However, the technique disclosed in Patent Literature 1 has a problem that the estimation using approximate curves focused only on spectral masking fails to correctly measure masking curves that significantly vary depending on individuals.

Furthermore, the above conventional techniques perform measurement by adjusting only one kind of acoustic properties. For example, Patent Literature 1 adjusts only the spectral gap width, and Non Patent Literature 2 adjusts only the presentation level of the probe. Therefore, these conventional techniques measure only one point on a masking curve. It is therefore necessary to perform a large number of measurements to enhance an accuracy of the estimation, which imposes temporal and physical burden on subjects.

In order to solve the above-described problems, an object of the present invention is to provide a hearing-ability measurement device and a hearing-ability measurement method which are capable of measuring a masking curve more correctly and in a shorter time.

Solution to Problem

In accordance with an aspect of the present invention for achieving the object, there is provided a hearing-ability measurement device that measures a hearing-ability of a subject, the hearing-ability measurements device including: a test sound generation unit configured to generate a test sound, the test sound including a probe and a masker; a test sound output unit configured to output the test sound generated by the test sound generation unit to the subject; a perception examination unit configured to examine whether or not the subject perceives the probe; and an adjustment unit configured to (i) when the perception examination unit determines that the subject perceives the probe, adjust at least one acoustic property from among acoustic properties including a spectral property of the masker, a temporal property of the masker, a sound pressure level of the masker, and a sound pressure level of the probe, so that the subject is less likely to perceive the probe, and (ii) when the perception examination unit determines that the subject does not perceive the probe, adjust the at least one acoustic property, so that the subject is more likely to perceive the probe, wherein the adjustment unit is configured to (i) when an examination result of the perception examination unit is same as a most-recent examination result, adjust the at least one acoustic property that is a most-recently adjusted acoustic property, and (ii) when the examination result of the perception examination unit is different from the most-recent examination result, adjust the at least one acoustic property from among the acoustic properties except a most-recently adjusted acoustic property, the test sound output unit is configured to output the test sound having the at least one acoustic property adjusted by the adjustment unit, and the hearing-ability measurement device measures the hearing-ability, by repeating a plurality of times the examination of the perception examination unit, the adjustment of the at least one acoustic property of the adjustment unit, and the output of the test sound of the test sound output unit.

With the above structure, it is possible to measure a masking curve more correctly and in a shorter time.

It is possible that the at least one acoustic property adjusted by the adjustment unit is a spectral gap width of the masker and a temporal gap width of the masker, and the adjustment unit is configured to: (i) decrease the temporal gap width, when the perception examination unit determines that the subject perceives the probe; and (ii) increase the spectral gap width, when the perception examination unit determines that the subject does not perceive the probe.

With the above structure, it is possible to measure a masking curve more correctly and in a shorter time.

It is also possible that the at least one acoustic property adjusted by the adjustment unit is a spectral gap width of the masker and a temporal gap width of the masker, and the adjustment unit is configured to: (i) decrease the spectral gap width, when the perception examination unit determines that the subject perceives the probe; and (ii) increase the temporal gap width, when the perception examination unit determines that the subject does not perceive the probe.

With the above structure, it is possible to measure a masking curve more correctly and in a shorter time.

It is further possible that the at least one acoustic property adjusted by the adjustment unit is a spectral gap width and/or a temporal gap width of the masker and a sound pressure level of the masker or the probe, and the adjustment unit is configured to: (i) decrease the sound pressure level, when the perception examination unit determines that the subject perceives the probe; and (ii) increase the spectral gap width and/or the temporal gap width, when the perception examination unit determines that the subject does not perceive the probe.

With the above structure, it is possible to measure a masking curve more correctly and in a shorter time.

It is still further possible that the at least one acoustic property adjusted by the adjustment unit is a spectral gap width and/or a temporal gap width of the masker and a sound pressure level of the masker or the probe, and the adjustment unit is configured to: (i) decrease the spectral gap width and/or the temporal gap width, when the perception examination unit determines that the subject perceives the probe; and (ii) increase the sound pressure level, when the perception examination unit determines that the subject does not perceive the probe.

With the above structure, it is possible to measure a masking curve more correctly and in a shorter time.

It is still further possible that when same examination results of the perception examination unit are obtained predetermined times, the adjustment unit is configured to adjust the at least one acoustic property so that the test sound becomes same as a test sound generated immediately prior to an examination result different from the examination results.

With the above structure, it is possible to measure a masking curve more correctly and in a shorter time.

It is still further possible that the perception examination unit includes an input unit configured to input information indicating whether or not the subject perceives the probe, and when the information indicating that the subject perceives the probe is inputted, the perception examination unit is configured to determine that the subject perceives the probe.

With the above structure, it is possible to measure a masking curve more correctly and in a shorter time.

It is still further possible that the perception examination unit is configured to determine that the subject perceives the probe, when the input unit inputs, successively twice, the information indicating that the subject perceives the probe, and the test sound output unit is configured to output the test sound that is same as a most-recent test sound, when the input unit inputs, only once, the information indicating that the subject perceives the probe.

With the above structure, it is possible to measure a masking curve more correctly and in a shorter time.

It is still further possible that the hearing-ability measurement device further includes a storage unit configured to store the acoustic properties of the test sound, and the hearing-ability measurement device estimates a masking curve of the subject from the acoustic properties stored in the storage unit.

With the above structure, it is possible to measure a masking curve more correctly and in a shorter time.

Advantageous Effects of Invention

According to the present invention, different kinds of acoustic properties are adjusted depending on whether or not a subject hears a probe. Therefore, without measuring each of points on a masking curve in the same manner as disclosed in the conventional methods, it is possible to directly track the masking curve. As a result, the masking curve can be measured more correctly and in a shorter time.

BRIEF DESCRIPTION OF DRAWINGS (a) in FIG. 1 is a schematic diagram showing a temporal masking curve where a time t is a variable. (b) in FIG. 1 is a schematic diagram showing a spectral masking curve where a frequency f is a variable. (c) in FIG. 1 is a schematic diagram showing a three-dimensional masking curve related to the temporal masking curve shown in (a) in FIG. 1 and the spectral masking curve shown in (b) in FIG. 1.

DESCRIPTION OF EMBODIMENTS

First of all, the basic principal of the present invention is described with reference to FIG. 1.

Figure 1:
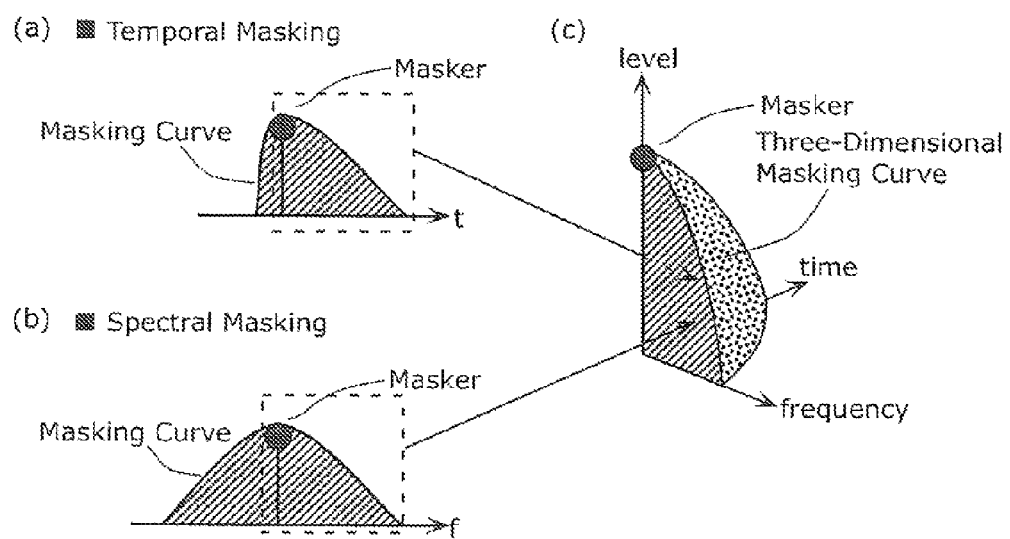

In FIG. 1, (a) is a schematic diagram showing a temporal masking curve where a time t is a variable. (b) in FIG. 1 is a schematic diagram showing a spectral masking curve where a frequency f is a variable. It is widely known that a subject does not perceive a sound with a power below the masking curve even if a time of presentation or frequency components are different from the ones of a masker.

By combining both temporal and spectral aspects of masking, it is possible to consider a three-dimensional masking curve as shown in (c) in FIG. 1.

Figure 2A:
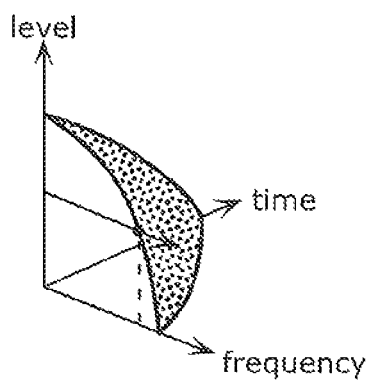
FIG. 2A is a schematic diagram showing principle of a conventional art disclosed in Patent Literature 1, by using the three-dimensional masking curve shown in (c) in FIG. 1.
Figure 2B:
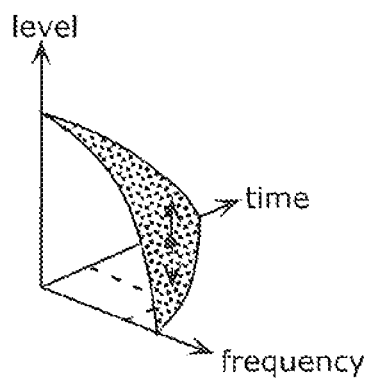
FIG. 2B is a schematic diagram showing principle of a conventional art disclosed in Patent Literature 2, by using the three-dimensional masking curve shown in (c) in FIG. 1.

By using the three-dimensional masking curve, one of the above-described conventional technologies can be explained as shown in (a) in FIG. 2. In the technique of Patent Literature 1, at predetermined presentation levels of the masker and the probe, a spectral gap width of a masker is increased until a subject perceives a probe. Therefore, the measurement is performed by adjusting acoustic property on a frequency-level plane as shown by an arrow in (a) in FIG. 2.

Moreover, in the technique disclosed in the conventional invention (Non Patent Literature 2), as shown in (b) in FIG. 2, at the predetermined masker presentation level, temporal gap width, and spectral gap width, the probe presentation level is increased if the subject doesn't perceive the probe, while the probe presentation level is decreased if the subject perceives it. Therefore, it is possible to consider that the measurement is performed by adjusting acoustic property under certain temporal and spectral conditions as shown by arrows in (b) in FIG. 2. Here, the spectral gap refers to a silent part generated on the frequency axis by using a band rejection filter or the like, and the temporal gap refers to a silent part generated on the time axis by using level adjustment or the like.

As described above, in the conventional techniques, the measurement is performed by adjusting one kind of acoustic property, such as a gap width or a probe presentation level, depending on a response of a subject. Therefore, the conventional techniques can measure only one point on a masking curve or a three-dimensional masking curve (hereinafter, referred to as a "masking curve").

Figure 3:
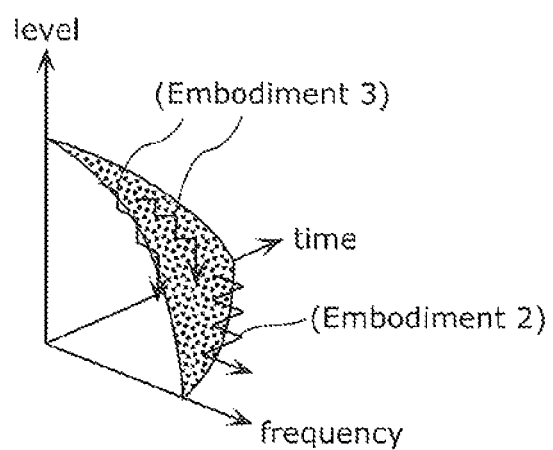
FIG. 3 is a schematic diagram showing principle of the present invention by using the three-dimensional masking curve shown in (c) in FIG. 1.

However, if different kinds of acoustic properties are adjusted depending on a response of the subject, it is possible to directly track the masking curve. For example, as shown in FIG. 3, the spectral gap of the masker is increased when the subject does not perceive the probe, and the temporal gap of the masker is decreased when the subject perceives the probe. As a result, it is possible to measure the masking curve in a shorter time and more correctly.

If other acoustic properties such as the probe presentation level and the masker presentation level as well as the masker spectral gap and the masker temporal gap of the masker are combined with each other, it is also possible to directly track the masking curve.

Figure 4A:
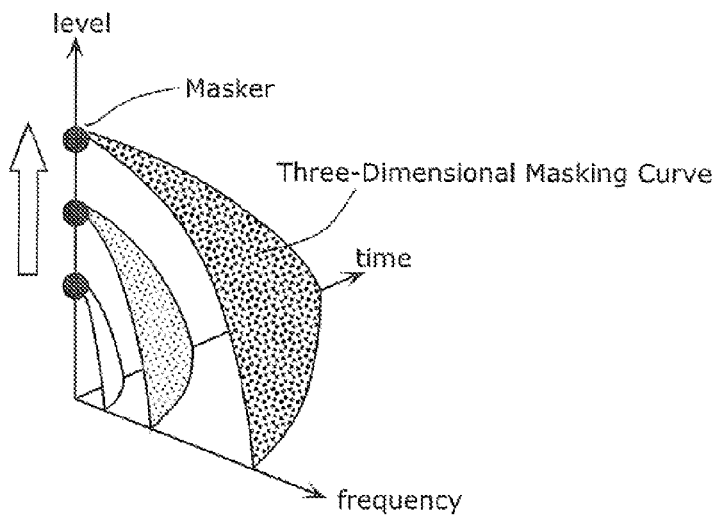
FIG. 4A is a schematic diagram showing changes in a three-dimensional masking curve caused by changes in a masker level.
Figure 4B:
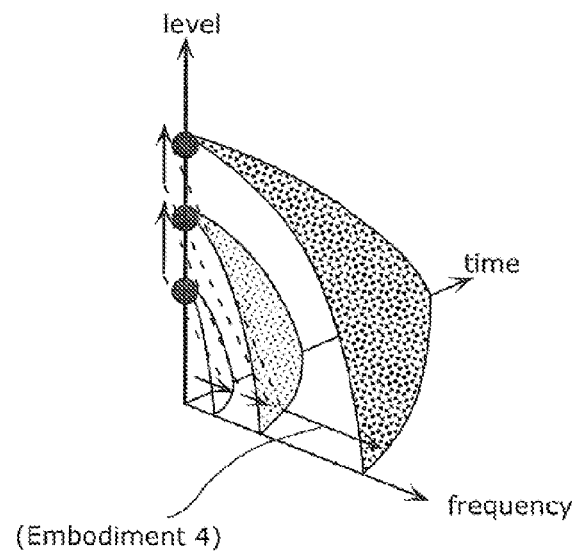
FIG. 4B is a schematic diagram showing principle of the present invention using a three-dimensional masking curve.

Moreover, as shown in (a) in FIG. 4, in Non Patent Literature 2, the shapes of the spectral and temporal masking curves change depending on the masker presentation level. Therefore, if different kinds of acoustic properties are adjusted depending on a response of the subject, it is possible to measure, at once, changes in the masking curve depending on the level. For example, as shown in (b) in FIG. 4, the masker spectral gap is increased when the subject cannot perceive the probe, and the masker presentation level is increased when the subject can perceive it. As a result, it is possible to measure the masking curve in a shorter time and more correctly.

The following describes embodiments of the prevent invention with reference to the corresponding figures. The same reference numerals are assigned to the identical units, so that explanation of the identical units is sometimes omitted. In addition, a value of each kind of acoustic property and a range of such a value are merely examples. They may be appropriately changed depending on a hearing-impaired degree, a demanded accuracy, a time restriction allowing measurement, and so on.

Embodiment 1

Figure 5:
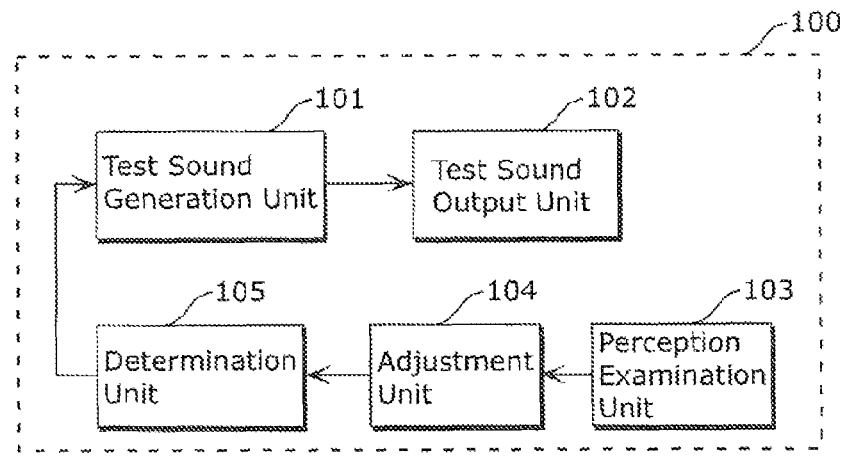
FIG. 5 is a block diagram showing a structure of a hearing-ability measurement device according to Embodiment 1.

FIG. 5 is a block diagram showing a structure of a hearing-ability measurement device 100 according to Embodiment 1.

The hearing-ability measurement device 100 includes a test sound generation unit 101 and a test sound output unit 102. The test sound generation unit 101 generates a test sound to be used in hearing-ability measurement. The test sound output unit 102 outputs the generated test sound. The hearing-ability measurement device 101 further includes a perception examination unit 103, an adjustment unit 104, and a determination unit 105. The perception examination unit 103 examines whether or not a subject perceives a probe included in the output test sound. The adjustment unit 104 adjusts acoustic properties of the test sound. The determination unit 105 determines whether or not the measurement is to be continued.

The test sound generation unit 101 generates a test sound that includes a probe and a masker. The probe and the masker have different predetermined acoustic properties. Here, the acoustic properties refer to properties such as a spectral property (center frequency, bandwidth, spectral gap width, and the like), a temporal property (time duration, temporal gap width, and the like), a sound pressure level, and the like of the prove or masker.

The test sound output unit 102 outputs the test sound generated by the test sound generation unit 101, from a headphone or the like.

The perception examination unit 103 examines whether or not the subject perceives the probe.

The adjustment unit 104 adjusts the acoustic properties of the test sound, based on the examination results of whether or not the subject perceives the probe.

The determination unit 105 determines, based on the acoustic properties, the number of repeated examinations, or the like, whether or not the measurement is to be ended.

Next, the measurement performed by the hearing-ability measurement device 100 is described with reference to FIG. 6.

Figure 6:
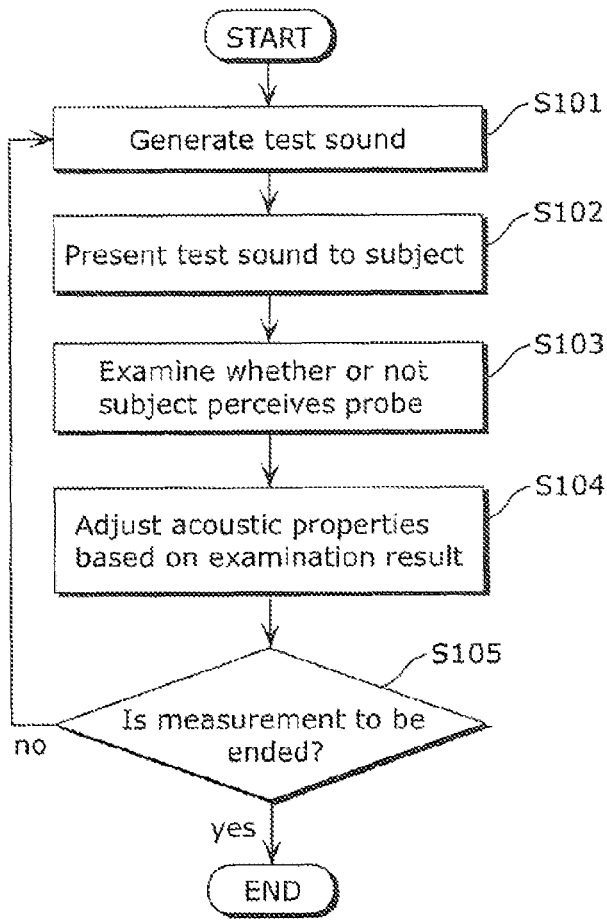
FIG. 6 is a flowchart of processing performed by the hearing-ability measurement device according to Embodiment 1.

FIG. 6 is a flowchart of the measurement performed by the hearing-ability measurement device.

The test sound generation unit 101 generates a test sound that includes at least one of a probe and a masker (Step S101).

The test sound output unit 102 outputs the generated test sound from a speaker, a headphone, or the like (Step S102).

Here, the presented test sound may be presented once in a designated time duration such as 0.1 to 10 seconds. It is also possible to present the test sound a plurality of times at designated time intervals, for example, every 0.1 to 2 seconds. It is also possible to combine the above presentation methods (hereinafter, each of these presentation is referred to as an "individually presentation method"). As described later, different test sounds may be presented at designated intervals. Here, the designated time duration and the designated time interval may be any numeral value that is realistic for measurement, for the subject. They are not limited to the above examples. Furthermore, if a method such as Bekesy Tracking disclosed in Non Patent Literature 3 is employed, the test sounds may be presented continuously (hereinafter, this presentation is referred to as a "continuous presentation method").

The perception examination unit 103 examines whether or not the subject perceives the probe (Step S103).

An example of the examination methods is that the test sound is presented once or a plurality of times, and the subject directly makes a: reply whether or not he/she can perceive the probe.

In another example, the subject keeps replying as perceiving while perceiving the probe, and keeps replying as not perceiving while not perceiving the prove.

The subject's reply may be made verbally, or using an interface by pressing a button, a touch panel or the like while perceiving. It is also possible to use any other objective methods such as brain wave measurement.

In a still another example of the examination methods, a sound including both of a probe and a masker and a sound including only the masker are presented in random order. Then, the subject makes a reply telling which he/she thinks includes the probe. In the examination, an examination result is made based on correctness of the reply. In this example, even the subject replying a random guess can make a correct reply at a certain rate. Therefore, a method such as a transformed up-down method may be used in the examination. For example, it is determined that the subject perceives the probe, if the subject makes successively correct replies predetermined times such as twice or more, but it is determined that the subject does not perceive the prove, if the subject makes one false reply.

Based on the examination result of the perception examination unit 103, the adjustment unit 104 adjusts one or more kinds of acoustic properties of the test sound (Step S104). Here, if it is determined that the subject perceives the probe, then the acoustic properties are adjusted so that the subject is less likely to perceive the probe. On the other hand, if it is determined that the subject doesn't perceive the probe, then the acoustic properties are adjusted so that the subject is more likely to perceive the probe. Furthermore, if the result of the examination as to whether or not the subject perceives the probe is the same as the most-recent examination result, then the adjustment unit 104 adjusts the same kinds of acoustic properties that have most-recently been adjusted. On the other hand, if the determination result is different from the most-recent examination result, then the adjustment unit 104 adjusts kinds of acoustic properties except the most-recently adjusted acoustic properties.

After adjusting the acoustic properties at Step S104, based on the adjusted acoustic properties, the number of repeated examinations, or the like, the determination unit 105 determines whether or not the measurement is to be ended (Step S105).

For example, if the adjusted acoustic properties exceed a predetermined range, the determination unit 105 determines that the measurement is to be ended. Or, if the number of measurements or a duration of the measurement exceeds a corresponding predetermined value, the determination unit 105 determines that the measurement is to be ended. If it is not determined that the measurement is to be ended, the processing returns to Step S101 to continue the measurement.

Figure 7:
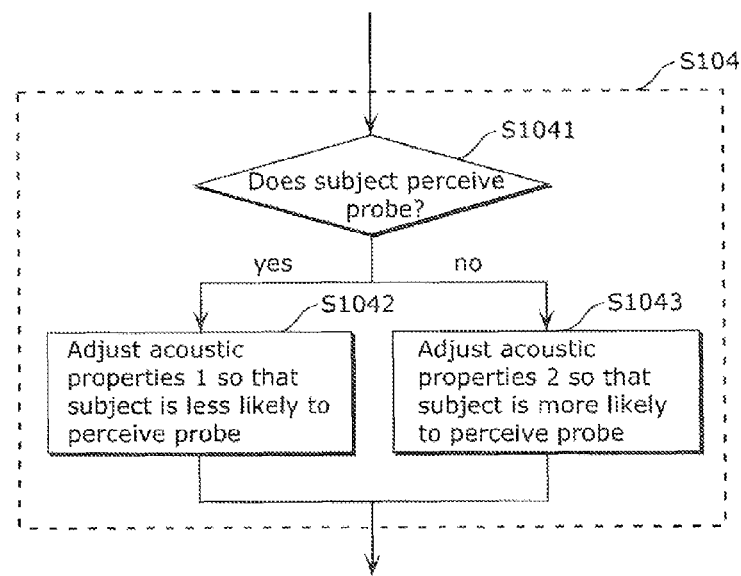
FIG. 7 is a flowchart of an example of acoustic property adjustment performed by the hearing-ability measurement device according to Embodiment 1.

An example of the adjustment at Step S104 is described with reference to FIG. 7. FIG. 7 is a flowchart of an example of the acoustic property adjustment performed by the hearing-ability measurement device.

If the perception examination unit 103 determines that the subject perceives the probe (Step S1041), then the adjustment unit 104 adjusts one or more kinds of acoustic properties (acoustic properties 1) so that the subject is less likely to perceive the probe (Step S1042). Here, the adjustment causing the subject to be less likely to perceive the probe means adjustment of the probe itself (decrease of the probe presentation level, decrease of the presentation time duration, or the like), or adjustment to increase a masking by the masker (increase of the masker presentation level, decrease of the spectral gap, decrease of the temporal gap, or the like).

On the other hand, if the perception examination unit 103 determines that the subject does not perceive the probe (Step S1041), then one or more acoustic properties (acoustic properties 2) different from the acoustic properties 1 adjusted at Step S1042 are adjusted to cause the subject to be more likely to perceive the probe (Step S1043). Here, the adjustment causing the subject to be more likely to perceive the probe means adjustment of the probe itself (increase of the probe presentation level, increase of the presentation time duration, or the like), or adjustment to reduce a masking by the masker (decrease of the masker presentation level, increase of the spectral gap, increase of the temporal gap, or the like).

In an example of the adjustment, at Step S1042, a spectral property or a temporal property is adjusted, and at Step S1043, a sound pressure level of the probe is adjusted. By repeating measurement including the above-described adjustment, it is possible to perform measurement along the masking curve. As a result, it is possible to measure a spectral masking curve or a temporal masking curve more correctly and at a higher speed.

In another example of the adjustment, at Step S1042, the spectral property is adjusted, and at Step S1043, the temporal property is adjusted. Or, at Step S1042, the temporal property is adjusted, and at Step S1043, the spectral property is adjusted. By repeating measurement including the above-described adjustment, it is possible to perform measurement along the masking curve. As a result, it is possible to measure the masking curve related to frequency and time more correctly and at a higher speed.

In still another example of the adjustment, at Step S1042, both the spectral property and the temporal property are adjusted, and at Step S1043, the sound pressure level of the probe is adjusted. By repeating measurement including the above-described adjustment, it is possible to measure the masking curve related to frequency and time at a higher speed.

In still another example of the adjustment, at Step S1042, one or both of the spectral property and the temporal property is/are adjusted at the same time, and at Step S1043, a sound pressure level of the masker is adjusted. By repeating measurement including the above-described adjustment, it is possible to measure a shape of the masking curve varying depending on the level at a higher speed.

Figure 8:
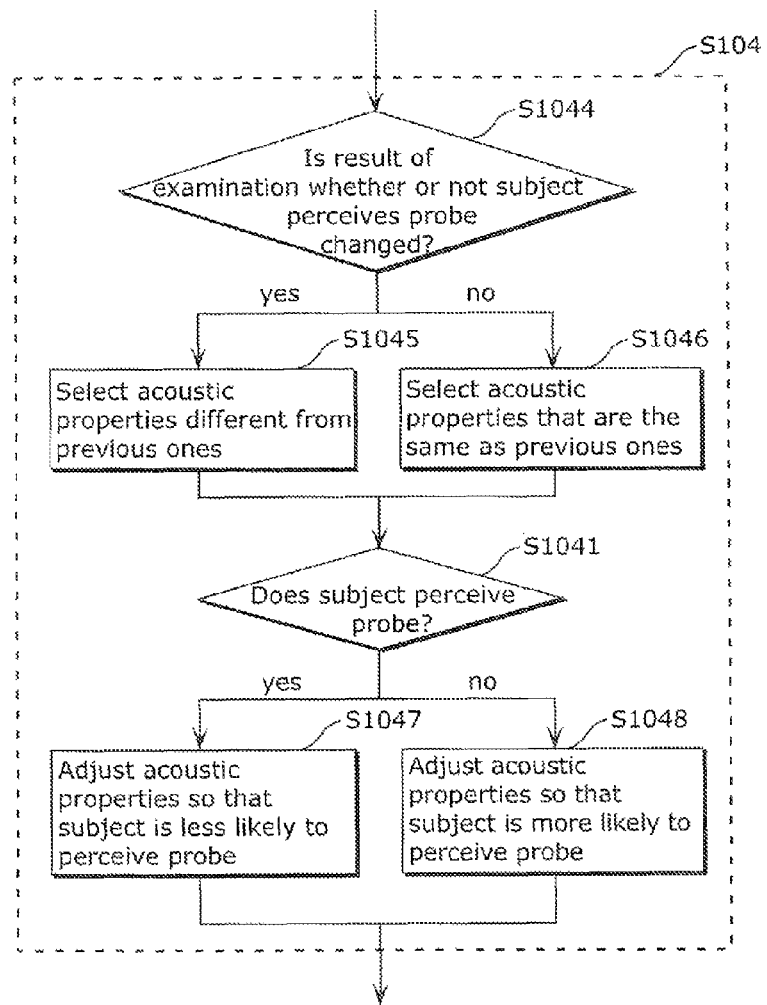
FIG. 8 is a flowchart of another example of the acoustic property adjustment performed by the hearing-ability measurement device according to Embodiment 1.

An example of the adjustment at Step S104 is described with reference to FIG. 8.

The perception examination unit 103 examines whether or not the subject perceives the probe (Step S1044). If the examination result is the same as the most-recent examination result (No at Step S1044), then the adjustment unit 104 selects the same acoustic properties as the previously-adjusted acoustic properties (Step S1046).

On the other hand, if the perception examination unit 103 examines whether or not the subject perceives the probe (Step S1044) and the examination result is different from the most-recent examination result (Yes at Step S1044), then the adjustment unit 104 selects acoustic properties at least one of which is different from the previously-adjusted acoustic properties (Step S1045).

It should be noted that, in the examination method using the above-described transformed up-down method, the same test sound is repeatedly presented without adjusting acoustic properties. For example, if it is not determined that the subject perceives the probe until the subject makes two successive correct replies, the acoustic properties are not adjusted after the first correct reply. It is also possible that a part (for example, approximately one-quarter to a half) of the acoustic properties is adjusted after the first correct reply, and then the remaining part of them is adjusted after the second correct reply.

Next, the perception examination unit 103 examines whether or not the subject perceives the probe (Step S1041). If it is determined that the subject perceives the probe (Yes at Step S1041), then the adjustment unit 104 adjusts the above-described selected acoustic properties so that the subject is less likely to perceive the probe (Step S1047).

On the other hand, if the perception examination unit 103 determines that the subject cannot perceive the probe (No at Step S1041), then the adjustment unit 104 adjusts the above-described selected acoustic properties so that the subject is more likely to perceive the probe (Step S1048).

As described above, the hearing-ability measurement device 100 adjusts different kinds of acoustic properties depending on the probe perception state of the subject. Therefore, without measuring each of points on a masking curve in the same manner as disclosed in the conventional methods, the hearing-ability measurement device 100 can directly track the masking curve. As a result, the hearing-ability measurement device 100 can measure the masking curve more Correctly and in a shorter time.

Embodiment 2

Figure 9:
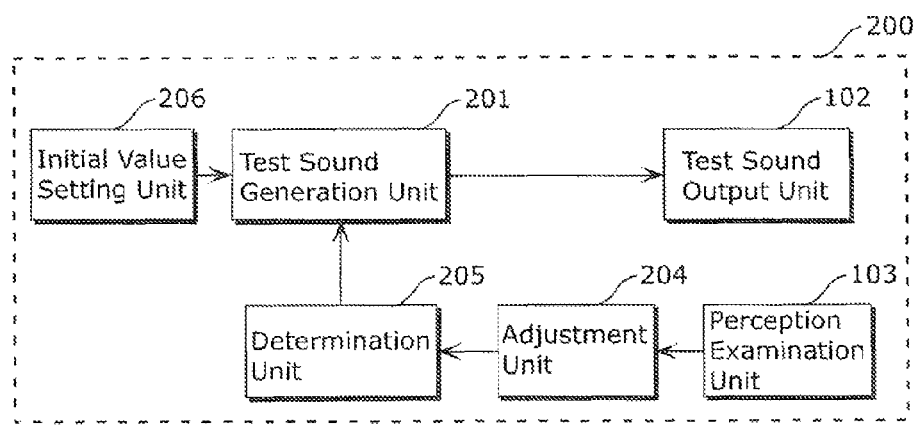
FIG. 9 is a block diagram showing a structure of a hearing-ability measurement device according to Embodiment 2.

FIG. 9 is a block diagram showing a structure of a hearing-ability measurement device 200 according to Embodiment 2.

The hearing-ability measurement device 200 includes a test sound generation unit 201, a test sound output unit 102, a perception examination unit 103, an adjustment unit 204, a determination unit 205, and an initial value setting unit 206. The test sound generation unit 201 generates a test sound to be used in hearing-ability measurement. The test sound output unit 102 outputs the generated test sound. The perception examination unit 103 examines whether or not the subject perceives the output test sound. The adjustment unit 204 adjusts the test sound. The determination unit 205 determines the adjustment of the test sound. The initial value setting unit 206 initializes the test sound.

Using acoustic properties adjusted by the adjustment unit, the test sound generation unit 201 generates a probe that is pure tone and a masker that is band noise. Then, the test sound generation unit 201 synthesizes the probe and the masker to generate the test sound.

The adjustment unit 204 adjusts acoustic properties of the masker, based on the examination result of whether or not the subject perceives the probe.

The determination unit 205 determines, based on the acoustic properties, the number of repeated examinations or the like, whether or not the measurement is to be ended.

The initial value setting unit 206 sets an initial value of each of the acoustic properties for each of the probe and the masker.

Next, the measurement performed by the hearing-ability measurement device 200 is described with reference to FIG. 10.

Figure 10:
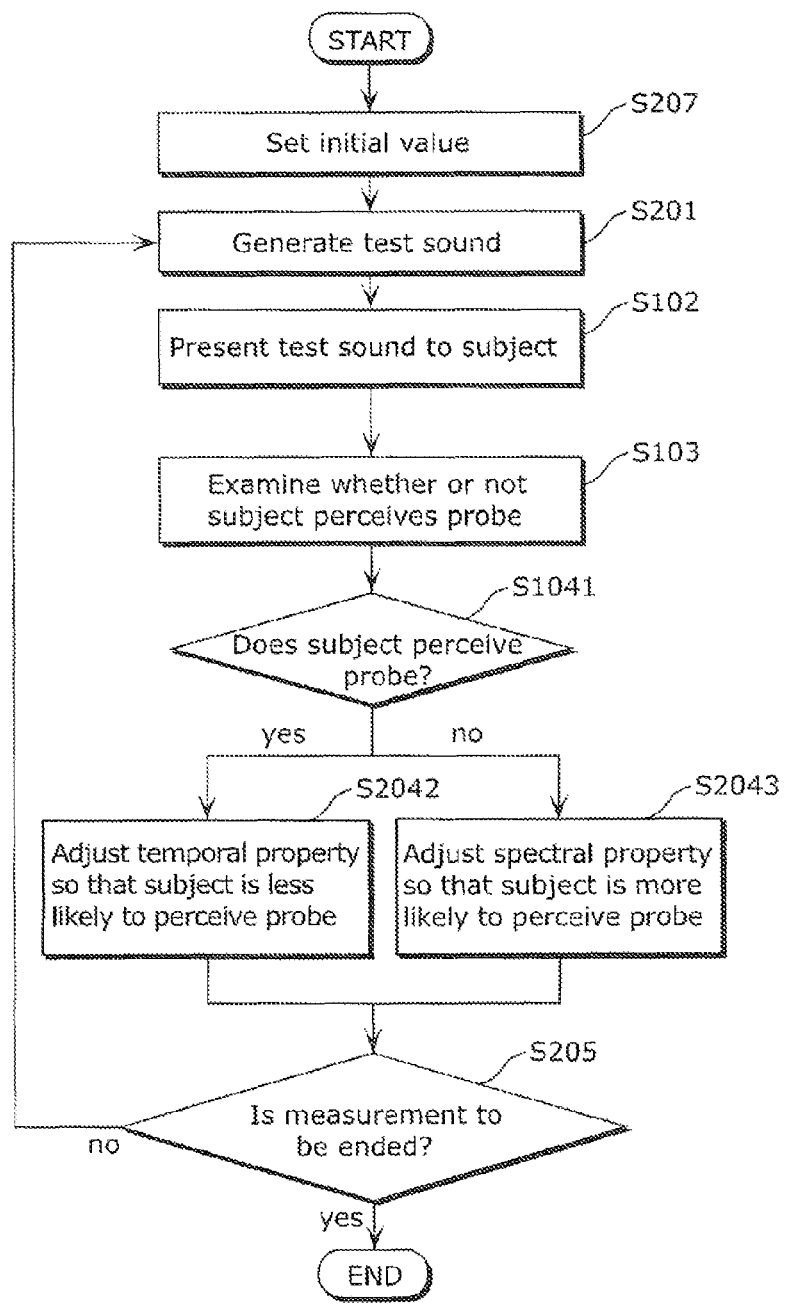
FIG. 10 is a flowchart of processing performed by the hearing-ability measurement device according to Embodiment 2.

FIG. 10 is a flowchart of the measurement.

Figure 11A:
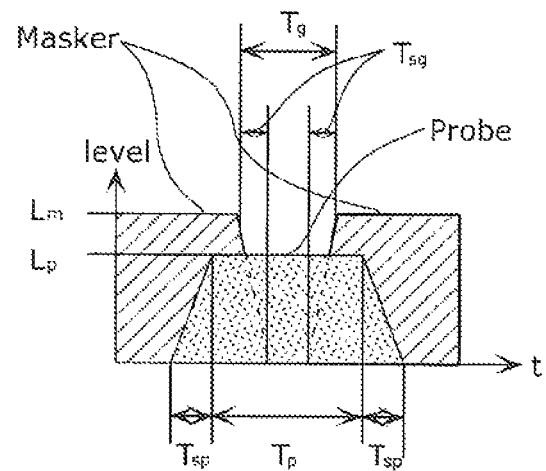
FIG. 11A is a graph plotting an acoustic signal and an acoustic property with respect to a time axis according to an embodiment of the present invention.
Figure 11B:
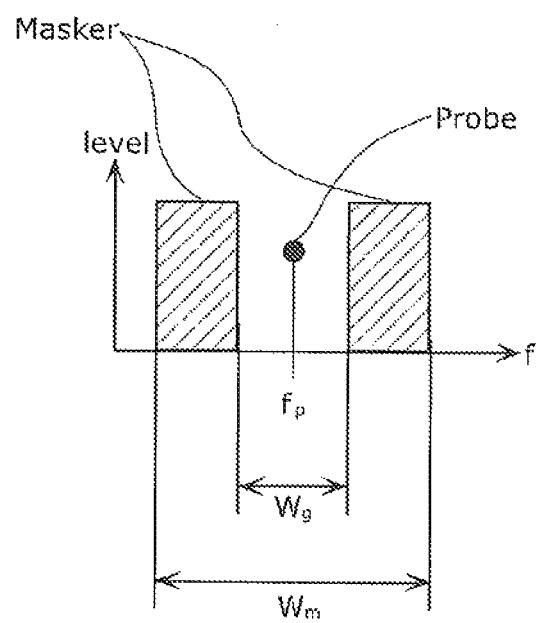
FIG. 11B is a graph plotting an acoustic signal and an acoustic property with respect to a frequency axis according to an embodiment of the present invention.

The initial value setting unit 206 sets an initial value of each of the acoustic properties for each of the probe and the masker (Step S207). The following explains the acoustic properties with reference to FIGS. 11A and 11B.

A presentation level $L_m$ of a masker (band noise) and a presentation level $L_p$ of a probe (pure tone) are set for current measurement. The levels are set in a range (from 0 dB to 120 dB) where a human being generally hears sound. In measurement for hearing-impaired people, it is sometimes necessary to set higher levels than the above.

A frequency $f_p$ of the probe is set to be a frequency to be measured. This frequency $f_p$ may be any frequency as far as it is within a range (from 20 Hz to 20000 Hz) where a human being can perceive the probe.

A time duration $T_p$ of the probe may be any as far as a human being can generally perceive the probe. For example, as disclosed in Non Patent Literature 2, the time duration $T_p$ may be set to 175 ms. Or, the sound may be a continuous sound.

A center frequency of the masker is set to be the same as the frequency $f_p$ of the probe. However, if asymmetry of the masker is to be measured, for example, the center frequency of the masker may be different from the frequency $f_p$ of the probe.

A bandwidth $W_m$ of the masker may be any bandwidth as far as it is enough to mask the probe. For example, as disclosed in Non Patent Literature 2, the bandwidth $W_m$ of the masker may be 1 octave or about a half octave. However, too narrow bandwidth $W_m$ makes it difficult to distinguish the masker from the pure tone in hearing. it is therefore desirable to set the bandwidth $W_m$ of the masker in a range allowing the distinction. However, if the bandwidth $W_m$ of the masker is set to be broad, it is possible to set the bandwidth $W_m$ of the masker to be broader than the spectral gap, or possible to use wide band noise without band limitation.

The spectral gap width $W_g$ of the masker is set to have a minimum value to be measured. For example, if the measurement is to start from the state without any spectral gap, the spectral gap width $W_g$ is set to 0 octave.

A temporal gap width $T_g$ of the masker is desirably set to have a duration allowing to perceive the probe under the conditions with the above-described masker presentation level, probe presentation level, and spectral gap width. For an example in the case of normal hearing people, the temporal gap width $T_g$ is preferably about 80 msec under the conditions with the masker presentation level of 70 dB, the probe presentation level of 20 dB, the probe frequency and masker center frequency of 1 kHz, and the spectral gap width of 0.1 octave. However, the values vary depending on a target subject, and are sometimes very high for hearing-impaired people. If it is difficult to previously set appropriate values, it is possible to set them to be the same or twice to three times higher than values of normal hearing people.

In addition, in order to prevent that a sudden change in the probe or masker presentation level causes undesired click sound, it is possible to add onset and offset ramps ($T_{sp}$, $T_{sg}$) for each of the probe and the masker. For example, as disclosed in Non Patent Literature 2, $T_{sp}$ may be set to 50 ms. Here, if the undesired click sound is to be masked by another masking noise, it is possible to set the onset and offset ramps to have shorter durations then the above, or possible to eliminate the onset and offset ramps (for example, set to 0 ms).

If, in the examination at Step S103 in FIG. 10, the perception examination unit 103 determines that the subject perceives the probe (Yes at Step S1041), then the adjustment unit 204 adjusts the temporal property so that the subject is less likely to perceive the probe (Step S2042). More specifically, the adjustment unit 204 shortens the temporal gap width $T_g$. An amount decreased from the current temporal gap width $T_g$ may have a predetermined value (for example, 10 msec) or a predetermined rate (for example, 10% of the current temporal gap width). Or, the temporal gap width $T_g$ may be set depending on an accuracy required in target measurement. For example, in the measurement for checking a rough shape of a masking curve, the above-described value may be higher. On the other hand, in the measurement for checking details of the masking curve, the above-described value may be lower.

On the other hand, if, in the examination at Step S103, the perception examination unit 103 determines that the subject does not perceive the probe (No at Step S1041), then the adjustment unit 204 adjusts the spectral property so that the subject is more likely to perceive the probe (Step S2043). More specifically, the spectral gap width $W_g$ is increased. Likewise Step S2042, an amount increased from the current spectral gap width $W_g$ may have a predetermined value (for example, 0.1 octave) or a predetermined rate (for example, 10% of the current spectral gap width). Or, likewise Step S2042, the spectral gap width $W_g$ may be set depending on an accuracy required in target measurement.

After adjusting the acoustic properties at Step S2042 or S2043, based on the adjusted acoustic properties, the number of repeated examinations, or the like, the determination unit 205 determines whether or not the measurement is to be ended (Step S205).

More specifically, if the temporal gap width has a low value (for example of normal hearing people, in a range about from 1 msec to 20 msec in which the temporal gap can be perceived), or the spectral gap width is increased (for example of normal hearing people, the spectral gap width is in a range about from 1 octave to 2 octaves in which the spectral masking does not occur, or in the case where the spectral gap width is close to a bandwidth of the masker), the determination unit 205 determines that the measurement is to be ended. Or, if the number of measurements or a time duration of the measurement exceeds a corresponding upper-limit value, the determination unit 205 determines that the measurement is to be ended. The upper-limit value of the number of measurements is, for example, set to be in a range approximately from 30 times to 300 times, and the upper-limit value of the measurement time duration is, for example, set to be in a range approximately from 5 minutes to 30 minutes. These upper-limit values may be set in considering subject's physical limitation or in order not to increase burden (hearing fatigue and the like) on the subject in the measurement.

If the measurement is determined to be ended at Step S205, further test sound is not generated and the measurement is ended. On the other hand, if the measurement is not determined to be ended at Step S205, the processing returns to Step S201 to continue the measurement.

As described above, the hearing-ability measurement device 200 decreases a temporal gap when the subject perceives a probe and increases a spectral gap when the subject does not perceive a probe. Therefore, without measuring each of points on a masking curve in the same manner as disclosed in the conventional methods, the hearing-ability measurement device 200 can directly track the masking curve. As a result, the hearing-ability measurement device 200 can measure the masking curve more correctly and in a shorter time.

It should be noted that it has been described above that a temporal gap is decreased when the perception examination unit 103 determines that the subject perceives a probe and a spectral gap is increased when the perception examination unit 103 determines that the subject does not perceive a probe. However, it is also possible that a spectral gap is decreased when it is determined that the subject perceives a probe and a temporal gap is increased when it is determined that the subject does not perceive a probe. In this case, the initial value setting unit 206 sets the temporal gap width to have a minimum value in a range to be measured, and sets the spectral gap width to have a value allowing probe perception.

It should also be noted that it has been described that a spectral gap is increased if it is determined that the prove is not perceived, but it is possible to increase a temporal gap width until the probe is firstly perceived after start of measurement. Thereby, it is possible to adoptively set an initial value of the temporal gap width, if it is difficult to previously set an appropriate initial value.

It is also possible that ranges of temporal and spectral gaps to be measured are previously set, then the initial value setting unit 206 sets their initial values (for example, a maximum value of the temporal gap width and a minimum value of the spectral gap width) in the respective ranges, and the determination unit 205 determines to end the measurement when the value exceeds the range.

Embodiment 3

Figure 12:
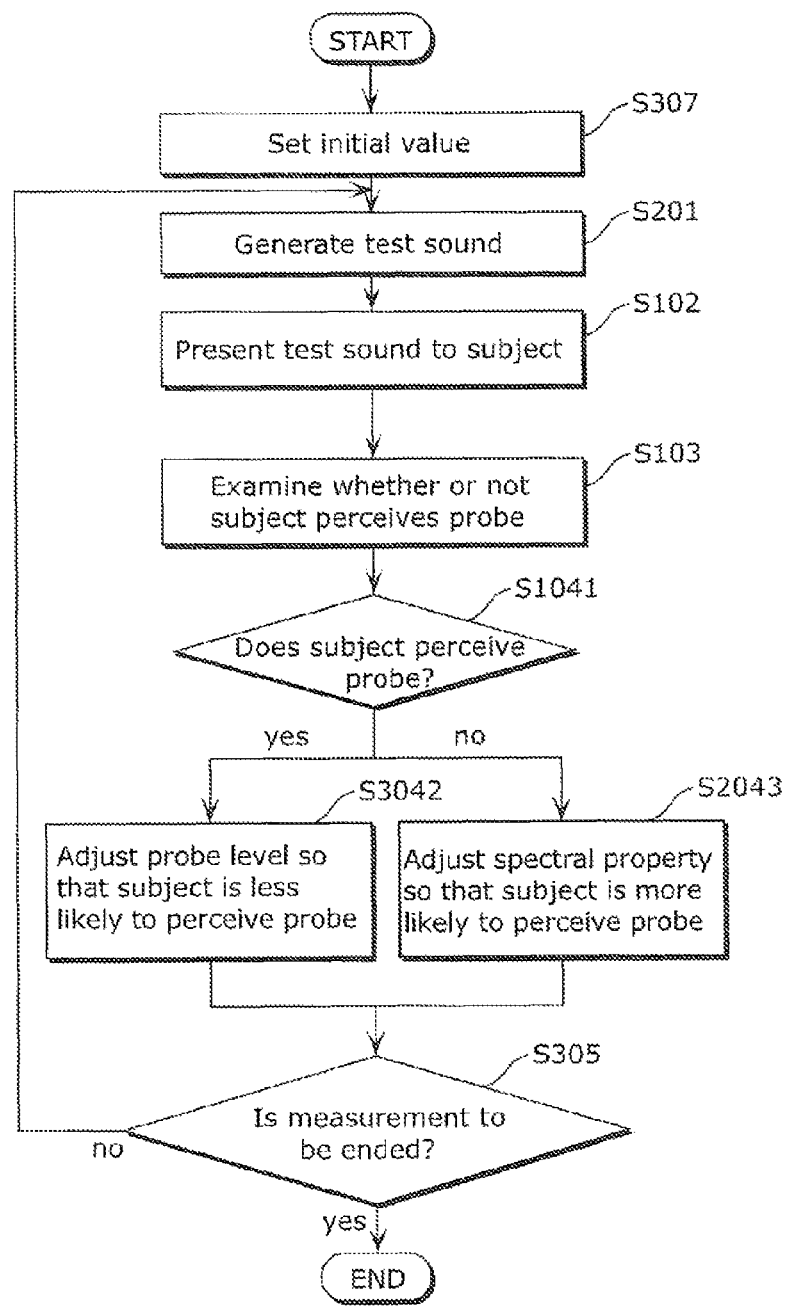
FIG. 12 is a flowchart of processing performed by a hearing-ability measurement device according to Embodiment 3.

Another example of the processing performed by the adjustment unit 204, the determination unit 205, and the initial value setting unit 206 in the hearing-ability measurement device 200 is described with reference to FIG. 12. FIG. 12 is a flowchart of steps in the adjustment performed by the hearing-ability measurement device 200

The initial value setting unit 206 sets an initial value of each of the acoustic properties for each of the probe and the masker as described below (Step S307).

The temporal gap width $T_g$ of the masker is set for measurement. If measurement related to a temporal masking is not necessary, the temporal gap width $T_g$ may be set to 0 msec (no temporal gap).

The presentation level $L_p$ of the probe (pure tone) is set to allow the probe to be perceived. For example, in the case of the masker presentation level of 70 dB, the prove presentation level $L_p$ is set to approximately 40 dB.

The other kinds of acoustic properties are set in the same manner as described in Embodiment 2.

The perception examination unit 103 examines whether or not the subject perceives the probe (Step S103). If it is determined that the subject perceives the probe (Yes at Step S1041), then the adjustment unit 204 adjusts the probe presentation level so that the subject is less likely to perceive the probe (Step S3042). More specifically, the probe presentation level $L_p$ is decreased. An amount decreased from the current level may have a predetermined value (for example, 0.5 dB), or a predetermined rate (for example, 10% of the current presentation level). Or, in the same manner as Step S2042, the probe presentation level $L_p$ may be set depending on an accuracy required in target measurement.

After adjusting the acoustic properties at Step S3042 or S2043, based on the adjusted acoustic properties or the number of repeated examinations, the determination unit 205 determines whether or not the measurement is to be ended (Step S305).

More specifically, if the probe presentation level is low (for example, a value close to 0 dB), or if the spectral gap width is broad (for example, a value close to a value of the masker bandwidth), the determination unit 205 determines the measurement is to be ended. Or, if the number of measurements or a time duration of the measurement exceeds a predetermined upper-limit level, the determination unit 205 determines that the measurement is to be ended, in the same manner as described at S205.

If the measurement is determined to be ended at Step S305, further test sound is not generated and the measurement is ended. On the other hand, if the measurement is not determined to be ended at Step S305, the processing returns to Step S201 to continue the measurement.

As described above, the hearing-ability measurement device 200 decreases the probe presentation level when the subject perceives probe and increases a spectral gap when the subject does not perceive the probe. Therefore, without measuring each of points on a masking curve in the same manner as disclosed in the conventional methods, the hearing-ability measurement device 200 can directly track the masking curve. As a result, the hearing-ability measurement device 200 can measure the masking curve more correctly and in a shorter time.

Although it has been described above that the spectral gap is increased when the perception examination unit 103 determines that the subject does not perceive a probe, it is also possible to increase the temporal gap as well as the spectral gap. In this case, the initial value setting unit 206 may set temporal gap width as well as the spectral gap width to have a minimum value in a range to be measured.

It should also be noted that it has been described above that the probe presentation level is decreased when the perception examination unit 103 determines that the subject perceives a probe and the spectral gap is increased when the perception examination unit 103 determines that the subject does not perceive the probe. However, it is also possible that the spectral gap is decreased when it is determined that the subject perceives the probe and the probe presentation level is increased when it is determined that the subject does not perceive the probe. In this case, the initial value setting unit 206 sets the probe presentation level to have a minimum value in a range to be measured, and sets the spectral gap width to have a value allowing probe perception. The same goes for the case where the temporal gap as well as the spectral gap are increased.

Embodiment 4

Figure 13:
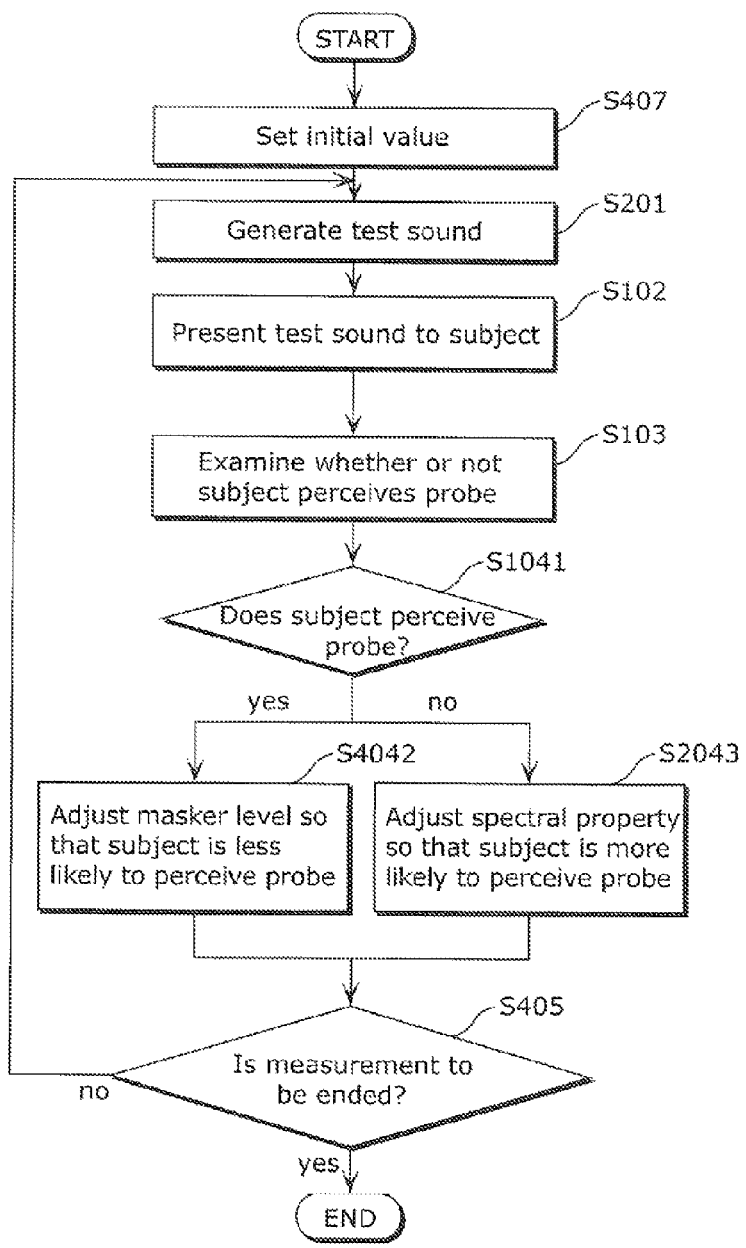
FIG. 13 is a flowchart of processing performed by a hearing-ability measurement device according to Embodiment 4.

Another example of the processing performed by the adjustment unit 204, the determination unit 205, and the initial value setting unit 206 in the hearing-ability measurement device 200 is described with reference to FIG. 13. FIG. 13 is a flowchart of another example of the steps in the adjustment performed by the hearing-ability measurement device 200.

The initial value setting unit 206 sets an initial value of each of the acoustic properties for each of the probe and the masker as described below (Step S407).

The temporal gap width $T_g$ of the masker is set for measurement. If measurement related to a temporal masking is not necessary, the temporal gap width $T_g$ may be set to 0 msec (no temporal gap).

The presentation level $L_p$ of the probe (pure tone) is set to allow the probe to be perceived. For example, when the masker presentation level is set to 70 dB, the prove presentation level $L_p$ is set to approximately 40 dB.

The other kinds of acoustic properties are set in the same manner as described in Embodiment 2.

If the perception examination unit 103 determines that the subject perceives the probe (Yes at Step S1041), then the adjustment unit 204 adjusts the masker presentation level so that the subject is less likely to perceive the probe (Step S4042). More specifically, the master presentation level $L_m$ is increased. An amount increased from the current level may have a predetermined value (for example, 0.5 dB), or a predetermined rate (for example, 10% of the current presentation level). Or, in the same manner as Step S2042, the masker presentation level $L_p$ may be set depending on an accuracy required in target measurement.

After adjusting the acoustic properties at Step S4042 or S2043, based on the adjusted acoustic properties or the number of repeated examinations, the determination unit 205 determines whether or not the measurement is to be ended (Step S405).

More specifically, if the probe presentation level is high (for example, a close to 100 dB), or if the spectral gap width is broad (for example, a value close to a value of the masker bandwidth), the determination unit 205 determines the measurement is to be ended. Or, if the number of measurements or a time duration of the measurement exceeds a predetermined upper-limit level, the determination unit 205 determines that the measurement is to be ended, in the same manner as described at S205.

If the measurement is determined to be ended at Step S405, further test sound is not generated and the measurement is ended. On the other hand, if the measurement is not determined to be ended at Step S405, the processing returns to Step S201 to continue the measurement.

As described above, the hearing-ability measurement device 200 increases the masker presentation level if the subject perceives a probe, and increases the spectral gap if the subject does not perceive the probe. Therefore, without measuring each of variations of the masking curve varying depending on a masker presentation level as disclosed in the conventional methods, the hearing-ability measurement device 200 can continuously measure the masking curve. As a result, the hearing-ability measurement device 200 can measure changes in a level of a masking curve more correctly and in a shorter time.

Although it has been described above that the spectral gap is increased when the perception examination unit 103 determines that the subject does not perceive a probe, it is also possible to increase the temporal gap as well as the spectral gap. In this case, the initial value setting unit 206 may set temporal gap width as well as the spectral gap width to have a minimum value in a range to be measured.

It should also be noted that it has been described above that the masker presentation level is increased when the perception examination unit 103 determines that the subject perceives the probe and the spectral gap is increased when the perception examination unit 103 determines that the subject does not perceives the probe. However, it is also possible that the spectral gap is decreased when it is determined that the subject perceives the probe and the masker presentation level is decreased when it is determined that the subject does not perceive the probe. In this case, the initial value setting unit 206 sets the masker presentation level to have a maximum value in a range to be measured, and sets the spectral gap width to have a value allowing probe perception. The same goes for the case where the temporal gap as well as the spectral gap are increased.

[Embodiment 5]

Figure 14:
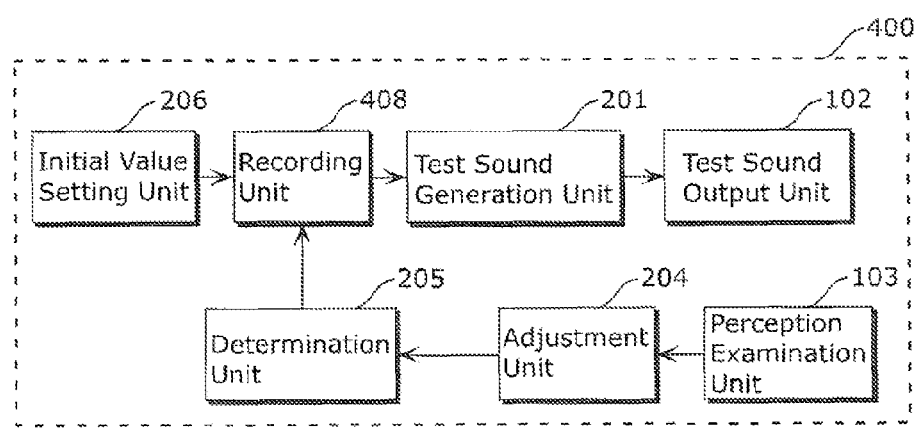
FIG. 14 is a block diagram showing a structure of a hearing-ability measurement device according to Embodiment 5.

FIG. 14 is a block diagram showing a structure of a hearing-ability measurement device 400 according to Embodiment 5.

The hearing-ability measurement device 400 further includes a recording unit 408 in addition to the structure of the hearing-ability measurement device 200 described in Embodiment 2. As shown in FIG. 14, the hearing-ability measurement device 400 includes an initial value setting unit 206, a recording unit 408, a test sound generation unit 201, a test sound output unit 102, a perception examination unit 103, an adjustment unit 204, and a determination unit 205.

The recording unit 408 receives and successively records acoustic properties set by the initial value setting unit 206. Or, if the determination, unit 205 does not determine that the measurement is to be ended, the recording unit 408 receives and successively records acoustic properties adjusted by the adjustment unit 204.

Next, the measurement performed by the hearing-ability measurement device 400 is described with reference to FIG. 10.

Figure 15:
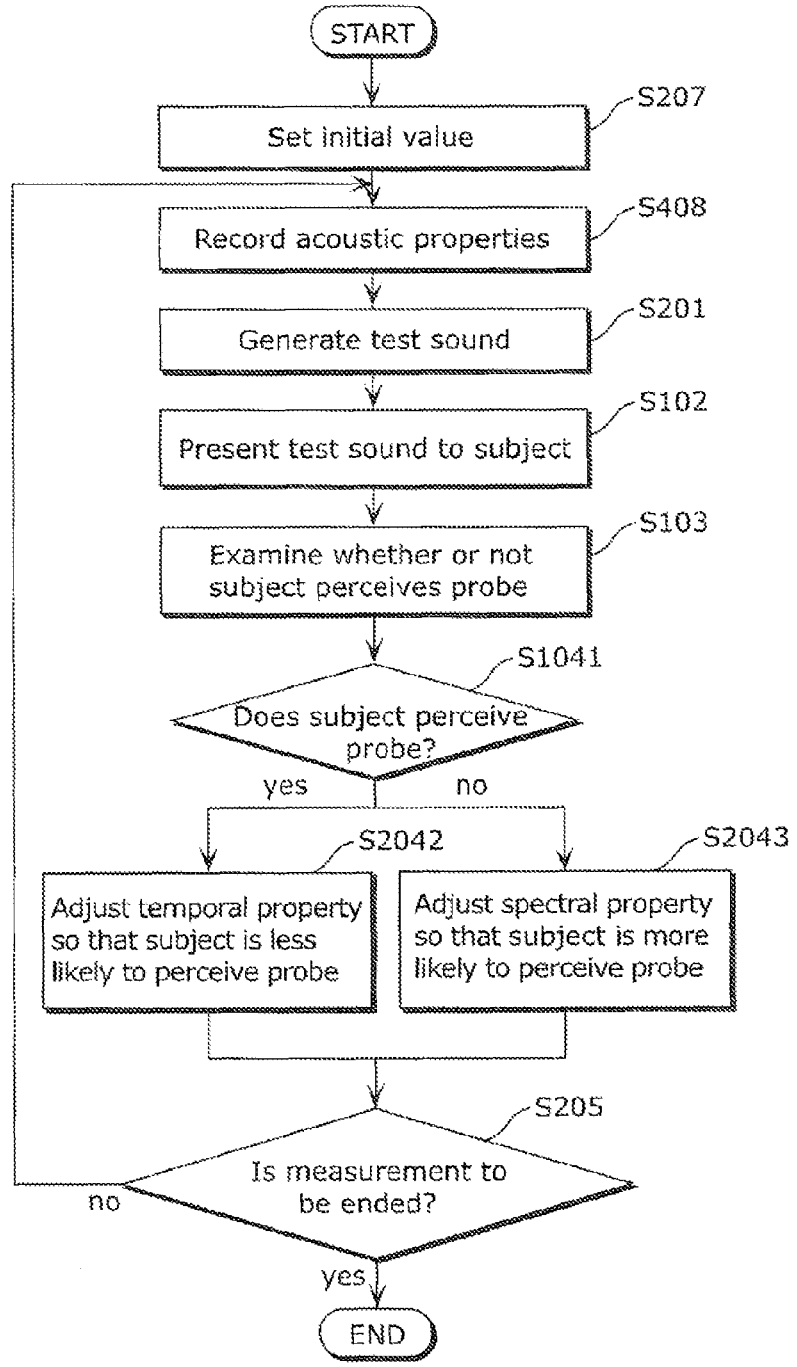
FIG. 15 is a flowchart of processing performed by the hearing-ability measurement device according to Embodiment 5.

FIG. 15 is a flowchart of steps in the adjustment performed by the hearing-ability measurement device 400.

After setting an initial value at Step S207, or when it is not determined at Step 205 that the measurement is to be ended, the set or adjusted acoustic properties are recorded at Step S408. It is also possible to record a difference caused by the adjustment.

More specifically, acoustic properties such as the frequency of the probe, the presentation levels of the probe and the masker, the spectral gap width, and the temporal gap width are successively recorded. Here, the above recording may be performed every time the setting or adjustment is performed, or performed only when a result of the examination as to whether the subject perceives a probe is different from the most-recent examination result.

Figure 16A:
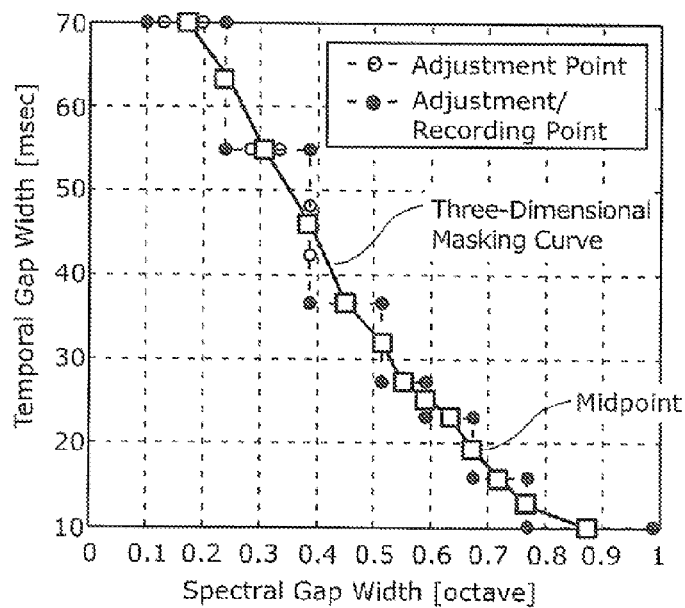
FIG. 16 is a graph plotting an example of adjustment logs for a spectral gap width and a temporal gap width.
FIG. 16B is a graph plotting a method of measuring masking curves.
Figure 16B:
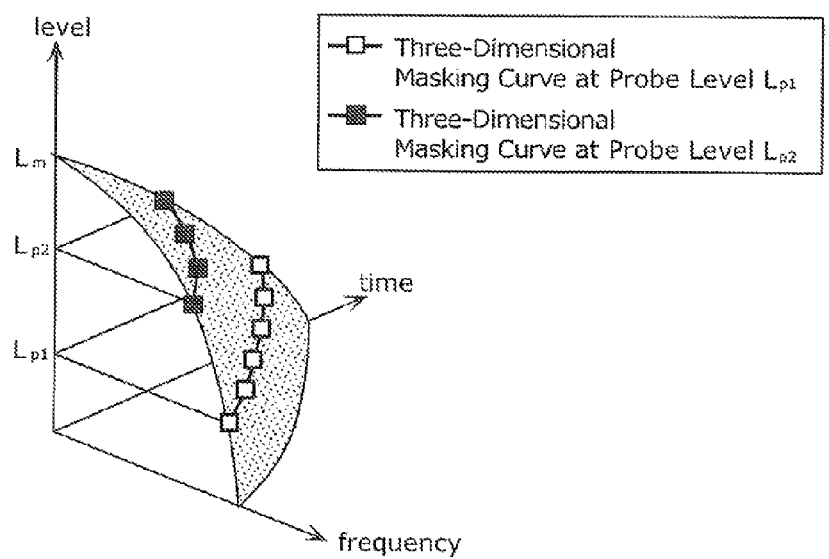

A masking curve can be estimated based on the recorded probe and masker presentation levels, spectral gap width, and temporal gap width. FIGS. 16A and 16B show an example of the estimation of a masking curve.

FIG. 16A shows a spectral gap width and a temporal gap width which are adjusted by the adjustment unit 204. Here, $L_m$ is the masker presentation level, and $Lp_1$ is the probe presentation level. The spectral gap width and the temporal gap width (an "adjustment point" and an "adjustment/recording point" in FIG. 16A) are adjusted based on a result of examination as to whether or not the subject perceives the probe. When the result of the examination is different from the most-recent examination result, the recording unit 408 performs recording (the "adjustment/recording point" in FIG. 16A). A masking curve is estimated by a line connecting midpoints between each pair of recorded points. Here, the line connecting the midpoints may be a straight line or a curve such as a spline curve. It is also possible to measure a masking curve by applying an approximate function (such as rounded-exponential function for spectral masking) to these midpoints.

FIG. 16B shows a masking curve at the masker level $L_m$. The masking curve measured by FIG. 16A corresponds a part along a surface of the level $L_{p1}$ of the masking curve. Likewise, when the probe level is set to a value such as $L_{p2}$ or the like to be measured, it is possible to estimate a masking curve along a different surface at the level $L_{p2}$ or the like, and increase an accuracy of the measurement of the entire masking curve.

As described above, since the recording unit 408 records acoustic properties required to measure a masking curve, the hearing-ability measurement device 400 can measure the masking curve more correctly and in a shorter time.

It should be noted that the situation where the spectral gap width and the temporal gap width are adjusted have been described above, but other situations where other kinds of acoustic properties are adjusted (for example, the probe presentation level and the spectral gap width are adjusted as described in Embodiment 3) can perform the same processing.

It should also be noted that the acoustic properties which are not adjusted by the adjustment unit 204 may be recorded only once after initialization at Step S207 or not recorded.

It should also be noted that it has been described that the recording unit 408 is included in the hearing-ability measurement device 400, it is also possible to use an external storage device.

In each of the above-described embodiments, if a plurality of examination results that a probe is perceived or a plurality of examination results that a probe is not perceived are successively Made and therefore the same acoustic properties are successively adjusted, the measurement may be continued after re-adjusting the acoustic properties.

Figure 17A:
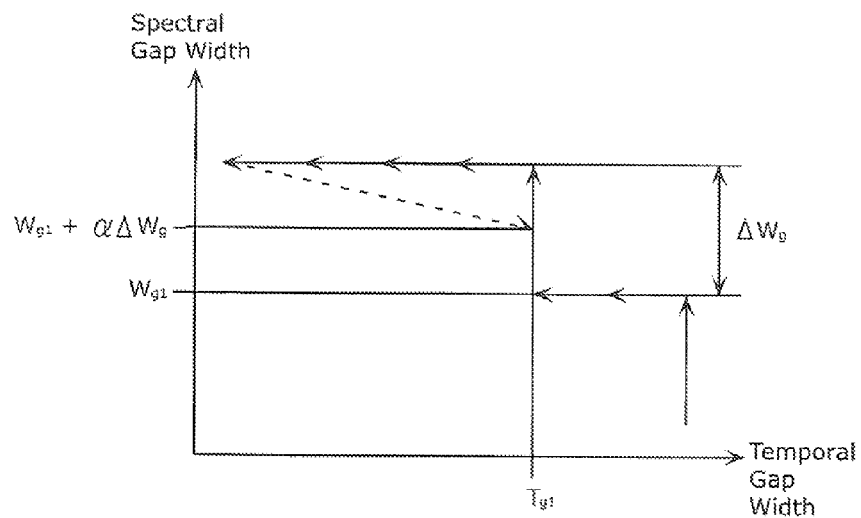
FIG. 17A is a graph plotting an example of re-adjustment of an acoustic property in the situation where examination results of perception success are successively made.
Figure 17B:
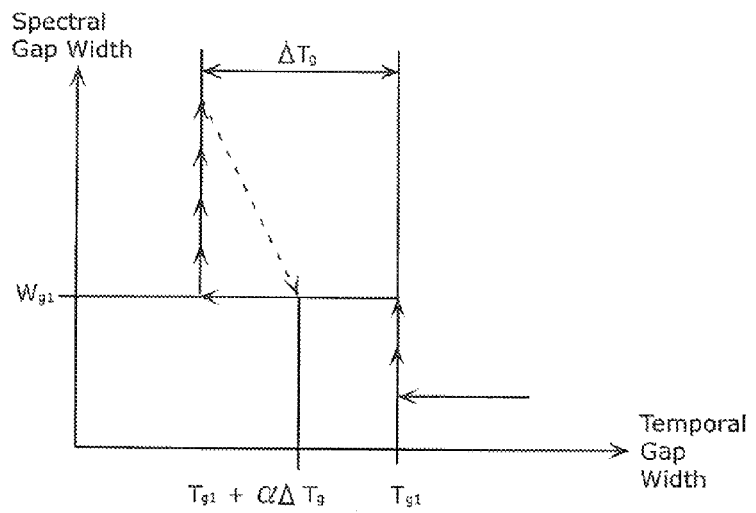
FIG. 17B is a graph plotting an example of re-adjustment of an acoustic property in the situation where examination results of perception failure are successively made.

An example of the processing according to Embodiment 2 is described with reference to FIGS. 17A and 17B. FIGS. 17A and 17B are graphs each showing changes in the temporal gap width and the spectral gap width.

If a plurality of examination results that the subject perceives a probe are successively made, then the temporal gap width is adjusted four successive times, and then a further examination result that the subject perceives a probe is made, the temporal gap width is adjusted to have a value $T_{g1}$ that is a value prior to the successive examination results, as shown by a broken line of FIG. 17A. Here, an adjustment amount $\Delta W_g$ of a spectral gap is multiplied by $\alpha$ (where $0<\alpha<1$). In addition, a spectral gap is adjusted to have a value ($W_{g1}+\alpha\Delta W_g$) that is a result of adding $\alpha\Delta W_g$ to a value $W_{g1}$ that is a value prior to a Previous examination result that the subject does not perceive the probe.

Likewise, if a plurality of examination results that the subject does not perceive a probe are successively made, then the spectral gap width is adjusted four successive times, and then a further examination result that the subject does not perceive a probe is made, the spectral gap width is adjusted to a value $W_{g1}$ that is a value prior to the successive examination results as shown by a broken line of FIG. 17B. Here, an adjustment amount $\Delta T_g$ of a temporal gap width is multiplied by a (where $0<\alpha<1$). In addition, the temporal gap is adjusted to have a value ($T_{g1}+\alpha\Delta T_g$) that is a result of adding $\alpha\Delta T_g$ to a value $T_{g1}$ that is a value prior to a previous examination result that the subject perceives the probe.

The same goes for the other embodiments. It should be noted that the situation where the same acoustic properties are adjusted for four successive times has been described above, but the number of successive adjustment may be changed to any other numbers more than one.

If the same examination results are successively made, it is considered that a most-recently adjusted amount is too large. Therefore, the acoustic properties are re-adjusted as described above, which makes it possible to autonomously optimize adjusted amounts to measure a masking curve in detail.

It is also possible to output the acoustic properties set by the initial value setting unit or adjusted by the adjustment unit to an external device (such as an adjustment device for a hearing aid or the like).

[Other Variations]

Although the present invention has been described using the above embodiments, the present invention is not limited to the above embodiment. The present invention may also be implemented as the followings.

(1) A part or all of the structural elements included in each of the above-described hearing-ability measurement devices may be implemented by a computer system including a microprocessor, a Read Only Memory (ROM), a Random Access Memory (RAM), a hard disk unit, and the like. The RAM or the hard disk unit holds a computer program for executing the same processing performed by each of the above-described hearing-ability measurement devices. The microprocessor is executed by the computer program to cause each of the hearing-ability measurement devices to perform the functions.

(2) A part or all of the structural elements included in each of the hearing-ability measurement devices according to the above-described embodiments may be implemented into a single Large Scale Integration (LSI). The system LSI is a super multi-function LSI that is a single chip into which a plurality of structural elements are integrated. More specifically, the system LSI is a computer system including a microprocessor, a ROM, a RAM, and the like. The RAM holds a computer program for executing the same processing performed by each of the above-described hearing-ability measurement devices. The microprocessor is executed by the computer program to cause the system LSI to perform its functions (3) A part or all of the structural elements included in each of the above-described hearing-ability measurement devices may be implemented into an Integrated Circuit (IC) card or a single module which is attachable to and removable from each of the devices. The IC card or the module is a computer system including a microprocessor, a ROM, a RAM, and the like. The IC card or the module may include the above-described super multi-function LSI. The microprocessor is executed by the computer program to cause the IC card or the module to perform its functions. The IC card or the module may have tamper resistance.

(4) The present invention may be implemented as a method realized by processing by the above-described computer. The present invention may also be a computer program causing the computer to execute the method, or digital signals indicating the computer program.

The present invention may be a computer-readable recording medium on which the computer program or the digital signals are recorded. Examples of the computer-readable recording medium are a flexible disk, a hard disk, a Compact Disc (CD)-ROM, a magnetooptic disk (MO), a Digital Versatile Disc (DVD), a DVD-ROM, a DVD-RAM, a BD (Blue-ray® Disc), and a semiconductor memory. The present invention may be digital signals recorded on the recording medium.

It should also be noted in the present invention that the computer program or the digital signals may be transmitted via an electric communication line, a wired or wireless communication line, a network represented by the Internet, data broadcasting, and the like.

It should also be noted that the present invention may be a computer system including a microprocessor and a memory. The memory may store the computer program, and the microprocessor may be executed by the computer program.

It should also be noted that the program or the digital signals may be recorded onto the recording medium to be transferred, or may be transmitted via a network or the like to be transferred, so that the program or the digital signals can be executed by a different independent computer system.

(5) The above-described embodiments and their variations may be combined.

INDUSTRIAL APPLICABILITY

As described above, according to the present invention, the hearing-ability measurement device and a method thereof can offer advantages of measuring a masking curve of a subject more correctly and in a shorter time. The present invention is suitable for adjustment and the like of devices emitting acoustic signals, such as hearing aids and audio devices.

REFERENCE SIGNS LIST

100, 200, 400 hearing-ability measurement device
101, 201 test sound generation unit
102 test sound output unit
103 perception examination unit
104, 204 adjustment unit
105, 205 determination unit
206 initial value setting unit
408 recording unit

The invention claimed is:

1. A hearing-ability measurement device that measures a hearing-ability of a subject, said hearing-ability measurement device comprising:
   a processor;
   a test sound generation unit configured to generate a test sound, the test sound including a probe and a masker;
   a test sound output unit configured to output the test sound generated by said test sound generation unit;
   a perception examination unit configured to examine, using the processor, whether or not the probe is perceived by the subject based on a received signal, the received signal indicating whether or not the probe is perceived by the subject; and
   an adjustment unit configured to
      (i) when said perception examination unit determines that the probe is perceived by the subject, adjust at least one acoustic property from among acoustic properties including a spectral property of the masker, a temporal property of the masker, a sound pressure level of the masker, and a sound pressure level of the probe, so that the likelihood that the probe is perceived by the subject after the at least one acoustic property is adjusted is less than the likelihood that the probe is perceived by the subject before the at least one acoustic property is adjusted, and
      (ii) when said perception examination unit determines that the probe is not perceived by the subject, adjust the at least one acoustic property, so that the likelihood that the probe is perceived by the subject after the at least one acoustic property is adjusted is more than the likelihood that the probe is perceived by the subject before the at least one acoustic property is adjusted
   wherein said adjustment unit is configured to
      (i) when an examination result of said perception examination unit is same as a most-recent examination result, adjust the at least one acoustic property that is a most-recently adjusted acoustic property, and
      (ii) when the examination result of said perception examination unit is different from the most-recent examination result, adjust the at least one acoustic property from among the acoustic properties except a most-recently adjusted acoustic property, said test sound output unit is configured to output the test sound having the at least one acoustic property adjusted by said adjustment unit, and said hearing-ability measurement device measures the hearing-ability, by repeating a plurality of times the examination of said perception examination unit, the adjustment of the at least one acoustic property of said adjustment unit, and the output of the test sound of said test sound output unit.

2. The hearing-ability measurement device according to claim 1,
wherein the at least one acoustic property adjusted by said adjustment unit is a spectral gap width of the masker and a temporal gap width of the masker, and
said adjustment unit is configured to:
(i) decrease the temporal gap width, when said perception examination unit determines that the probe is perceived by the subject; and
(ii) increase the spectral gap width, when said perception examination unit determines that the probe is not perceived by the subject.

3. The hearing-ability measurement device according to claim 1,
wherein the at least one acoustic property adjusted by said adjustment unit is a spectral gap width of the masker and a temporal gap width of the masker, and
said adjustment unit is configured to:
(i) decrease the spectral gap width, when said perception examination unit determines that the probe is perceived by the subject; and
(ii) increase the temporal gap width, when said perception examination unit determines that the probe is not perceived by the subject.

4. The hearing-ability measurement device according to claim 1,
wherein the at least one acoustic property adjusted by said adjustment unit is (a) at least one of a spectral gap width and a temporal gap width of the masker and (b) a sound pressure level of one of the masker and the probe, and
said adjustment unit is configured to:
(i) decrease the sound pressure level, when said perception examination unit determines that the probe is perceived by the subject; and
(ii) increase the at least one of the spectral gap width and the temporal gap width, when said perception examination unit determines that the probe is not perceived by the subject.

5. The hearing-ability measurement device according to claim 1,
wherein the at least one acoustic property adjusted by said adjustment unit is (a) at least one of a spectral gap width and a temporal gap width of the masker and (b) a sound pressure level of one of the masker and the probe, and
said adjustment unit is configured to:
(i) decrease the at least one of the spectral gap width and the temporal gap width, when said perception examination unit determines that the probe is perceived by the subject perceives; and
(ii) increase the sound pressure level, when said perception examination unit determines that the probe is not perceived by the subject.

6. The hearing-ability measurement device according to claim 1,
wherein, when same examination results of said perception examination unit are obtained predetermined times, said adjustment unit is configured to adjust the at least one acoustic property so that the test sound becomes same as a test sound generated immediately prior to an examination result different from the examination results.

7. The hearing-ability measurement device according to claim 1,
wherein said perception examination unit includes
an input unit configured to receive the received signal indicating whether or not the probe is perceived by the subject, and
when the received signal indicates that the probe is perceived by the subject is inputted, said perception examination unit is configured to determine that the probe is perceived by the subject.

8. The hearing-ability measurement device according to claim 7,
wherein said perception examination unit is configured to determine that the probe is perceived by the subject, when said input unit receives, successively twice, the received signal indicating that the probe is perceived by the subject, and
said test sound output unit is configured to output the test sound that is same as a most-recent test sound, when said input unit receives, only once, the received signal indicating that the probe is perceived by the subject.

9. The hearing-ability measurement device according to claim 1, further comprising
a storage unit configured to store the acoustic properties of the test sound, and
said hearing-ability measurement device estimates a masking curve of the subject from the acoustic properties stored in said storage unit.

10. A hearing-ability measurement method of measuring a hearing-ability of a subject, said hearing-ability measurement method comprising:
generating a test sound including a probe and a masker;
outputting the test sound generated in said generating;
examining, using a processor, whether or not the probe is perceived by the subject based on a received signal, the received signal indicating whether or not the probe is perceived by the subject; and
(i) when it is determined in said examining that the subject perceives the probe, adjusting at least one acoustic property from among acoustic properties including a spectral property of the masker, a temporal property of the masker, a sound pressure level of the masker, and a sound pressure level of the probe, so that the likelihood that the probe is perceived by the subject after the at least one acoustic property is adjusted is less than the likelihood that the probe is perceived by the subject before the at least one acoustic property is adjusted, and
(ii) when it is determined in said examining that the subject does not perceive the probe, adjusting the at least one acoustic property, so that the likelihood that the probe is perceived by the subject after the at least one acoustic property is adjusted is more than the likelihood that the probe is perceived by the subject before the at least one acoustic property is adjusted,
wherein, in said adjusting of the at least one acoustic property,
(i) when an examination result of said examining is same as a most-recent examination result, the at least one acoustic property that is a most-recently adjusted acoustic property is adjusted, and
(ii) when the examination result of said examining is different from the most-recent examination result, the at least one acoustic property from among the acoustic properties except a most-recently adjusted acoustic property is adjusted, in said outputting, the test sound having the at least one acoustic property adjusted in said adjusting is outputted, and the hearing-ability is measured by repeating a plurality of times said examining, said adjusting, and said outputting.

11. A non-transitory computer-readable recording medium for use in a computer, said recording medium having a computer program recorded thereon for causing the computer to execute a hearing-ability measurement method of measuring a hearing-ability of a subject, and the program causing the computer to execute:

generating a test sound including a probe and a masker;

outputting the test sound generated in said generating;

examining whether or not the probe is perceived by the subject based on a received signal, the received signal indicating whether or not the probe is perceived by the subject; and (i) when it is determined in said examining that the subject perceives the probe, adjusting at least one acoustic property from among acoustic properties including a spectral property of the masker, a temporal property of the masker, a sound pressure level of the masker, and a sound pressure level of the probe, so that the likelihood that the probe is perceived by the subject after the at least one acoustic property is adjusted is less than the likelihood that the probe is perceived by the subject before the at least one acoustic property is adjusted, and (ii) when it is determined in said examining that the subject does not perceive the probe, adjusting the at least one acoustic property, so that the likelihood that the probe is perceived by the subject after the at least one acoustic property is adjusted is more than the likelihood that the probe is perceived by the subject before the at least one acoustic property is adjusted, wherein, in said adjusting of the at least one acoustic property, (i) when an examination result of said examining is same as a most-recent examination result, the at least one acoustic property that is a most-recently adjusted acoustic property is adjusted, and (ii) when the examination result of said examining is different from the most-recent examination result, the at least one acoustic property from among the acoustic properties except a most-recently adjusted acoustic property is adjusted, in said outputting, the test sound having the at least one acoustic property adjusted in said adjusting is outputting, and the hearing-ability is measured by repeating a plurality of times said examining, said adjusting, and said outputting.

12. A hearing-ability measurement device that measures a hearing-ability of a subject, said hearing-ability measurement device comprising:

a processor; and a non-transitory memory having stored thereon executable instructions, which when executed by the processor, cause the processor to perform:

generating a test sound including a probe and a masker;

outputting the test sound generated in said generating;

examining whether or not the probe is perceived by the subject based on a received signal, the received signal indicating whether or not the probe is perceived by the subject; and (i) when it is determined in said examining that the subject perceives the probe, adjusting at least one acoustic property from among acoustic properties including a spectral property of the masker, a temporal property of the masker, a sound pressure level of the masker, and a sound pressure level of the probe, so that the likelihood that the probe is perceived by the subject after the at least one acoustic property is adjusted is less than the likelihood that the probe is perceived by the subject before the at least one acoustic property is adjusted, and (ii) when it is determined in said examining that the subject does not perceive the probe, adjusting the at least one acoustic property, so that the likelihood that the probe is perceived by the subject after the at least one acoustic property is adjusted is more than the likelihood that the probe is perceived by the subject before the at least one acoustic property is adjusted, wherein, in said adjusting of the at least one acoustic property, (i) when an examination result of said examining is same as a most-recent examination result, the at least one acoustic property that is a most-recently adjusted acoustic property is adjusted, and (ii) when the examination result of said examining is different from the most-recent examination result, the at least one acoustic property from among the acoustic properties except a most-recently adjusted acoustic property is adjusted, in said outputting, the test sound having the at least one acoustic property adjusted in said adjusting is outputting, and the hearing-ability is measured by repeating a plurality of times said examining, said adjusting, and said outputting.

* * * * *